(12) United States Patent
Tatarkiewicz et al.

(10) Patent No.: US 10,598,586 B1
(45) Date of Patent: Mar. 24, 2020

(54) APPARATUS AND METHOD FOR ANALYZING PARTICLES

(71) Applicant: HORIBA Instruments Incorporated, Irvine, CA (US)

(72) Inventors: Jan J. Tatarkiewicz, San Diego, CA (US); Miroslav Pejcinovic, Lake Forrest, CA (US)

(73) Assignee: HORIBA INSTRUMENTS INCORPORATED, Irvine, CA (US)

( * ) Notice: Subject to any disclaimer, the term of this patent is extended or adjusted under 35 U.S.C. 154(b) by 0 days.

(21) Appl. No.: 16/528,044

(22) Filed: Jul. 31, 2019

(51) Int. Cl.
*G01N 15/14* (2006.01)

(52) U.S. Cl.
CPC . *G01N 15/1434* (2013.01); *G01N 2015/1493* (2013.01); *G01N 2015/1497* (2013.01)

(58) Field of Classification Search
CPC ....... G01N 15/1434; G01N 2015/1493; G01N 2015/1497; G01N 15/1436; G01N 15/1404; G01N 21/03; G01N 15/1463; G01N 2015/0038
USPC ................................. 356/335, 342, 246, 336
See application file for complete search history.

(56) References Cited

U.S. PATENT DOCUMENTS

| 5,641,457 | A | * | 6/1997 | Vardanega | B01L 1/04 250/461.2 |
|---|---|---|---|---|---|
| 7,772,005 | B1 | * | 8/2010 | Squires | A61K 35/52 422/73 |
| 8,004,661 | B2 | * | 8/2011 | Luscher | G01N 15/1404 356/72 |
| 2004/0008867 | A1 | * | 1/2004 | Fein | G01N 21/6458 382/100 |
| 2008/0225066 | A1 | * | 9/2008 | Yorimoto | B41J 29/38 347/14 |
| 2014/0193172 | A1 | * | 7/2014 | Tawada | G03G 21/0029 399/111 |
| 2014/0329022 | A1 | * | 11/2014 | Otani | B05D 1/06 427/485 |
| 2019/0263665 | A1 | * | 8/2019 | Newman | C01B 32/26 |

FOREIGN PATENT DOCUMENTS

WO  WO-2017196410 A1 * 11/2017 ............. C01B 32/26

* cited by examiner

*Primary Examiner* — Isiaka O Akanbi
(74) *Attorney, Agent, or Firm* — Micheal de la Cerra

(57) ABSTRACT

A particle image analyzer is disclosed that includes a transparent moving structure with a load surface and an opposite surface, where a portion of the load surface is constructed to adhere particles. A particle discharge nozzle deposits particles on the load surface and an image sensor positioned adjacent to the load surface takes images of the particles as they move past the image sensor. A light source positioned adjacent to the opposite surface illuminates the particles imaged by the image sensor. The light from the light source defines an illumination path that travels from the light source, through the opposite surface, through the load surface and to the image sensor.

21 Claims, 3 Drawing Sheets

APPARATUS AND METHOD FOR ANALYZING PARTICLES

1.0 TECHNICAL FIELD

The present invention relates to a system for analyzing the size and shape of particles.

2.0 RELATED APPLICATIONS

None

3.0 BACKGROUND

Bright field microscopy, where a digital video camera observes particles from a direction perpendicular to an illuminated background surface, is used to detect the size and shape of particles with diameters smaller than a few millimeters down to a few microns. When examining particles in dry particulate samples, prior art teaches using a sample feed where particles are either falling or are moved by compressed air to scatter the particles, such as what is presented in Annex C of ISO application 13322-2:2006, titled Particle size analysis—Image analysis methods—Part 2: Dynamic image analysis methods, incorporated herein by reference. In that Annex C, several examples of sample feeds for bright field microscopy applications are provided: a sheath flow cell, a free-falling system, and the measurement of particles on a moving substrate or at a conveyor discharge point.

A sheath flow cell, which is the most commonly used method, involves forming a sheath with high pressure air that separates particles so that they do not obstruct one another in front of the digital camera. When measuring particles on a moving substrate, there is a particle dispenser moving over the substrate (e.g. a glass plate), while the camera scans the entire area of the substrate, which is illuminated from underneath. Free falling systems or measurement of particles at a conveyor discharge point are not popular methods, due to the lack of precision and control in how the particles are separated, and therefore are rarely deployed in practice. All the above methods present the fundamental problem of particle movement during exposure, which can create fuzziness in the image, depending on the speed at which the particles are moving.

As a non-limiting example, a digital camera may have 5-micron by 5-micron pixels and 2× zoom that allows for the visualization of sub-millimeter particles on a 2000-pixel by 1000-sensor, which corresponds to an optical system with a calibration constant of 2.5 microns per pixel linear size. If a short exposure of 100 microseconds is used, the speed of moving a distance of one pixel is equivalent to 2.5 cm/sec. This is a very low speed when compared to free falling speed in Earth's gravitational field, which results in about 2 m/sec speed after just 20 cm is traveled by particles. Moreover, if high pressure air is being used to separate the particles to form a sheath, the obtained speeds are even higher. In some commercial apparatus, the speed can be up to 50 m/sec, thus requiring very short exposure times to not result in fuzzy images, and which thus requires very high intensity illumination to capture clear images. The intensity of light required would have to be high power laser light sources that are technically difficult.

What is needed, therefore, is a particle analyzer that overcomes these shortcomings.

4.0 SUMMARY

A system for analyzing the size and shape of particles is disclosed. A particle image analyzer is disclosed that includes a transparent moving structure with a load surface and an opposite surface, where a portion of the load surface is constructed to adhere particles. A particle discharge nozzle deposits particles on the load surface, and an image sensor positioned adjacent to the load surface takes images of the particles as they move past the image sensor. A light source positioned adjacent to the opposite surface illuminates the particles imaged by the image sensor. The light from the light source defines an illumination path that travels from the light source, through the opposite surface, through the load surface and to the image sensor.

The load surface may include an adhesive or an electrostatic generator.

The transparent moving structure may include a transparent belt wrapped around a front roller and a back roller. These may further include an electrostatic generator positioned prior to the particle discharge nozzle so as to impart a positive charge to a region of the load surface prior to the deposition of particles on the load surface. A ground may be positioned after the imager so as to release the particles from the load surface. The analyzer may have a particle recovery basis that collects particle that have been release from the load surface.

The transparent moving structure may include a transparent platter that is rotated by a platter motor. The particle discharge nozzle may be constructed to move laterally across the load surface of the platter, such that the platter rotation and the lateral movement of the discharge nozzle create a spiral particle deposition pattern on the load surface. In such case, the image sensor should also be constructed to move laterally across the load surface of the platter. Additionally, the light source sensor may be constructed to move laterally across the opposite surface of the platter following sensor movements.

The analyzer may include a processor connected to various components in the analyzer. For example, it may be connected to the image sensor so as to receive images from the sensor and to control the image sensor parameters and the image sensor's lateral movement across the load surface. The processor may also be connected to the light source and controls the light source and any lateral movement of the light source across the opposite surface. The processor may also be connected to the particle discharge nozzle and may also control the deposition rate of the nozzle, along with any lateral movement of the discharge nozzle across the load surface. The processor may also control the electrostatic generator. The transparent moving structure may include a motor that is also controlled by the processor.

Additional aspects, alternatives and variations, as would be apparent to persons of skill in the art, are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

6.0 DETAILED DESCRIPTION

Figure 1:
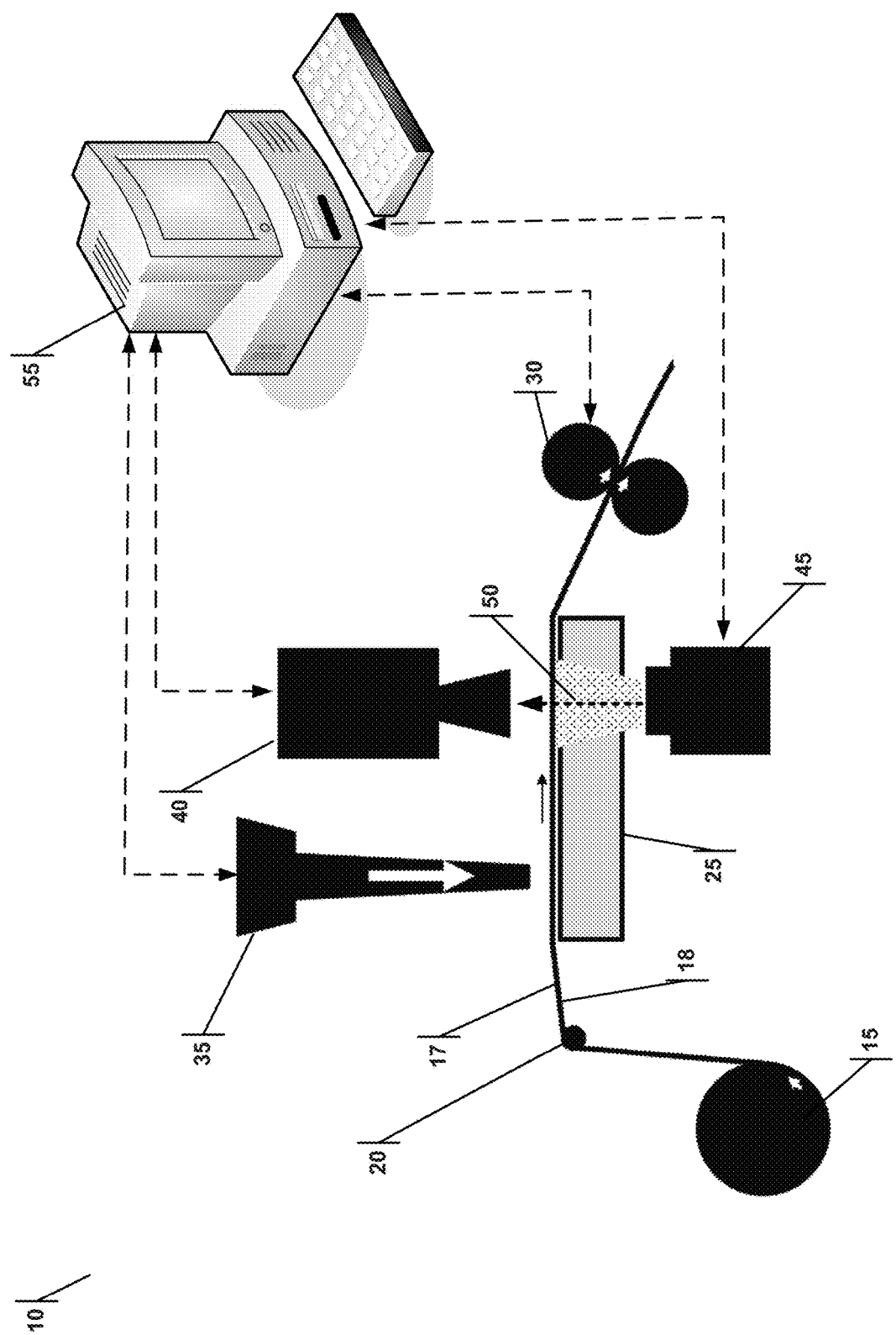
FIG. 1 illustrates a first embodiment of a particle image analyzer.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents, as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms, unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with attached figures and is provided for ease of reference, where like reference numerals designate corresponding features throughout the specification and figures:

Particle Image Analyzer (1st embodiment) 10
Transparent Sticky Belt/Tape 15
Sticky Side Load Surface 17
Opposite Surface 18
Guide Roller 20
Transparent Bed 25
Pull Rollers 30
Particle Discharge Nozzle 35
Image Sensor 40
Light Source 45
Illumination Path 50
Processor 55
Particle Image Analyzer (2nd embodiment) 110
Front Roller 115
Transparent Belt/Tape 120
Back Roller 125
Electrostatic Generator 130
Ground 135
Particle Recovery Basin 140
Particle Image Analyzer (3st embodiment) 210
Transparent Platter 215
Platter Motor 220
Platter Rotation 225
Particle Deposition Spiral 230
Particle Discharge Nozzle Lateral Movement 235
Image Sensor Lateral movement 240
Light Source Lateral Movement 245

In a first embodiment of a particle image analyzer, as shown in FIG. 1, the particle image analyzer includes a light source 45, an image sensor 40, a particle discharge nozzle 35, and a transparent moving structure 15 with a load surface 17 and an opposite surface 18. The particle discharge nozzle 35 deposits particles on the load surface 17, and at least a portion of the load surface 17 is constructed in such a way so as to have particles adhere to the surface. The load surface 17 may be considered a moving substrate, and may be moved at a considerable speed to enable particle spatial separation. Because it adheres particles to the surface 17, the particles stay put on that surface and may be imaged with more ease, as the linear speed of the moving substrate may be much lower than what can be achieved in the prior art, and the fuzziness of images during short exposure times can be eliminated. The particles may be adhered to the load surface 17 by having the surface constructed of an adhesive tape.

As illustrated in FIG. 1, the particle image analyzer 10 may involve the use of a transparent sticky belt or tape 15 being moved by rollers, including one or more guide rollers 20 and pull rollers 30. The top side of the transparent sticky belt/tape 15, where the particle discharge nozzle 35 deposits particles, is considered the load surface 17, and the underside of the transparent sticky belt/tape 15 is considered the opposite surface 18. The particle discharge nozzle 35 may optionally vibrate or be exposed to ultrasounds to separate the particles before it discharges them onto the load surface 17. There may be a transparent bed 25 that supports the moving belt/tape substrate from below. After the particles are deposited by the particle discharge nozzle 35, they can travel and scatter over a distance before reaching the image sensor 40. The transparent bed 25 is illuminated by a light source 45, which provides an illumination path 50 from the light source 45 through the opposite surface 18 and through the load surface 17 to the image sensor 40. When the particles reach the illumination path 50, the image sensor 40 positioned adjacent to the load surface 17 can take images of the particles as they move past the image sensor 40. It should be noted that the term image sensor need not refer to a singular image sensor, but may refer to a group of multiple sensors or even an array or arrays of sensors. Such a plurality of sensors would be an obvious modification to one of skill in the art and would not change the function of the image sensor, and thus such a variation is entirely in the spirit and scope of the invention.

The particle image analyzer 10 may also comprise a processor 55 that can be used to control the particle discharge nozzle 35, the image sensor 40, the pull rollers 30, and the light source 45. The processor 55 is connected to the image sensor 40 and receives images from the sensor 40. It may also control the parameters of the image sensor 40 to calibrate the sensor and control the settings. The processor 55 can connect to the light source 45 and may turn the light source 45 on and off and can optionally vary the light intensity of the light source 45. The processor 55 may be connected to the particle discharge nozzle 35 and may control the rate of deposition by the particle discharge nozzle 35. Finally, the processor 55 may control a motor that in turn moves the transparent sticky belt/tape 15 via the pull rollers 30, and may control the speed of the belt/tape 15 by controlling the motor.

In FIG. 1, the embodiment illustrated makes use of adhesives to adhere the particles to the load surface 17. Such an adhesive surface can be very robust in maintaining particles at their positions so that the particles do not move even though the substrate moves, but the use of adhesive does not allow for sample recovery. Using electrostatic methods is much more technologically complicated and can be applied only to the dielectric particles and not metallic ones (electrostatic induction), but the particle sample can be recovered after imaging or measurement, which is an advantage.

Figure 2:
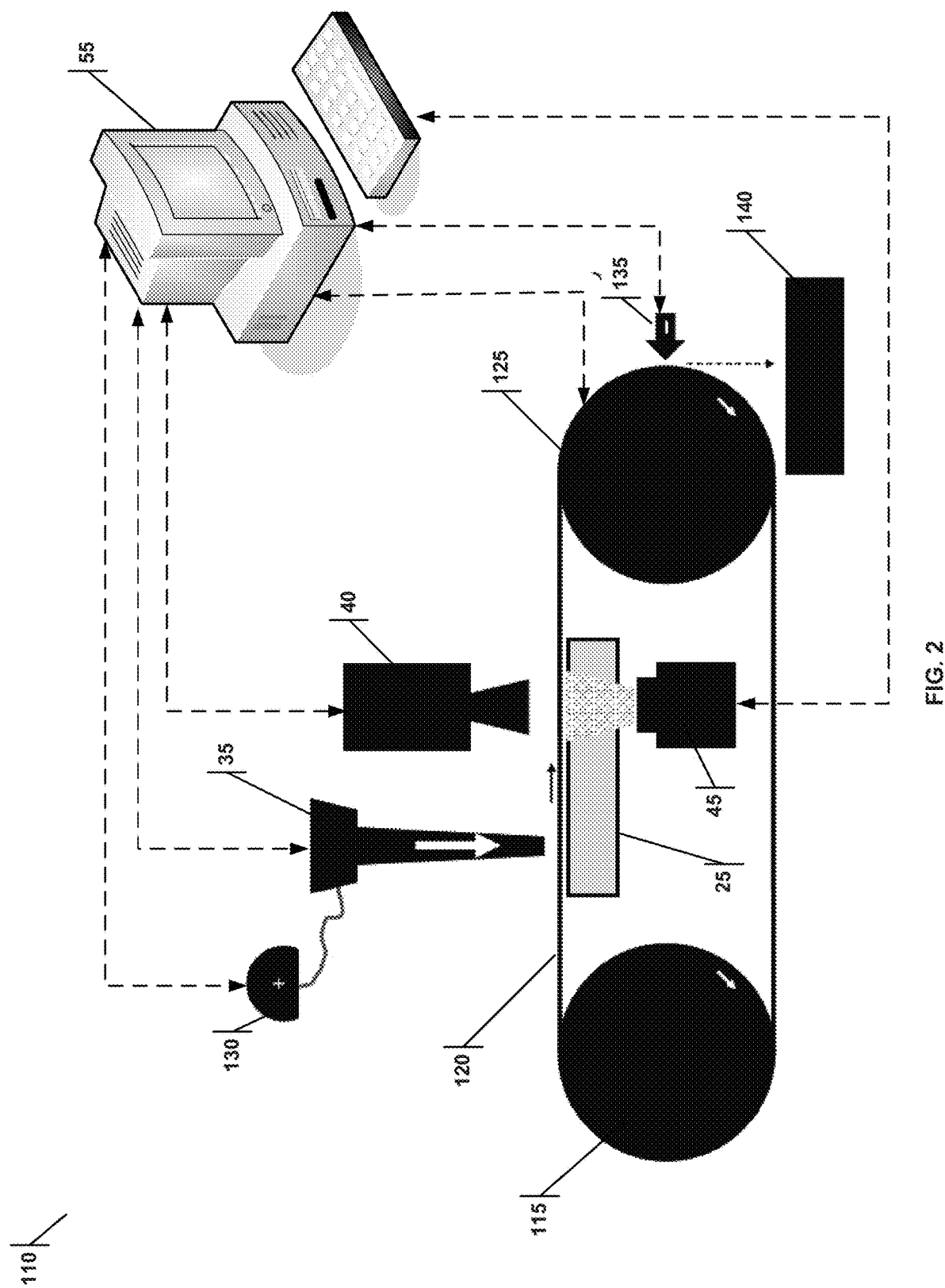
FIG. 2 illustrates a second embodiment of a particle image analyzer.

FIG. 2 shows a particle image analyzer 110 that utilizes electrostatic methods for adhering particles onto a moving surface of the transparent belt/tape 120. Here, the transparent moving structure comprises a transparent belt/tape 120 wrapped around a front roller 115 and a back roller 125. The particle image analyzer 110 also comprises an electrostatic generator 130 (shown as a positive generator) that is positioned prior to the particle discharge nozzle 35 so as to impart a charge to a region of the load surface prior to the deposition of particles onto the load surface of the transparent belt/tape 120. The particles stay motionless relative to the load surface by virtue of electrostatic forces, and the tape with particles retained moves over the transparent table 25 into the illumination region/path 50 created by the light source 45, and the image sensor 40 positioned adjacent to the load surface takes images of the particles as they move past.

The front roller 115 feeds the moving transparent belt/tape 120, and the back roller 125 accepts and moves the moving transparent belt/tape 120. Optionally, the particle image analyzer 110 may have a grounded line 135 that by removing the charge from the belt 120 releases the particles from the load surface. The particles may then be released into a particle recovery basin, which collects particles that have been released from the load surface.

Here, some estimates of practical parameters involved in the design of the particle image analyzer are discussed, so as to impart better understanding of the advantages.

TABLE 1

Estimated Parameters of Roiling Tape Embodiments

| Tape speed: | | |
|---|---|---|
| pixel effective size | 2.5 μm | |
|  | 0.0000025 m | |
| exposure | 0.1 msec | 100 μsec |
|  | 0.0001 sec | |
| 1 pix during exposure | 0.0250 m/sec | |
|  | 2.50 cm/sec | |
| sample of | 5000 particles | |
| max particle diameter | 1 mm | |
| tape length | 5.00 m | |
| tape rolling time | 200.00 sec | |
|  | 3.33 min | |

Assuming an exposure time of 0.1 msec as before and particles of 1 mm diameter, for a statistically relevant sample size such as 5000 particles, if the particles are arranged linearly, the minimal tape length for a non-overlapping arrangement of particles must be at least 5 m long. With the speed that assures sharp, clear images (calculated as 2.5 cm/sec; see Background), a measurement time of 200 seconds or 3.33 minutes is needed, which is a reasonable time for such a measurement. However, this estimate assumes that the particles can be discharged fairly slowly; to not have overlapping or stacking of particles, less than 25 such large particles must be deposited per second. This can be a problem if the particles are made out of polished, smooth material like steel or glass. Assuming non-overlap with faster discharge speed and larger particle sizes, the tape should be moved at a faster speed, thus compromising the sharpness of the recorded images. This problem can be resolved by using a rotating platter with spiral deposition of particles, where deposition occurs at a higher rotational speed, while the images are subsequently recorded at a much lower speed (see Table 2).

TABLE 2

Estimated Parameters of Platter Embodiments

| Disc speed: | |
|---|---|
| Disc speed: | |
| track thickness | 0.75 cm |
| inner spiral radius | 2.5 cm |
| outer spiral radius | 12.5 cm |
| spiral length | 628.4 cm |
| number of turns | 13.3 |
| average circle length | 47.25 cm |
| time per revolution | 18.90 sec |
|  | 0.31 min |
| total scanning time | 251.36 sec |
|  | 4.19 min |

Assuming a platter of an outer diameter of 25 cm, and an inner diameter of 5 cm, where the center of the platter is used to connect to a rotating motor, and assuming a track thickness of 7.5 mm, such a platter can accommodate a spiral of over 6 m long (about 13 turns). The average single circle length would be about 45 cm, so for a 2.5 cm/sec linear speed, the platter will have to make each revolution in about 19 seconds for a total measurement time of about 4 minutes to capture the image. However, one has to remember that for deposition, the platter can be rotated much faster, thus preventing the stacking or overlap of particles.

Figure 3:
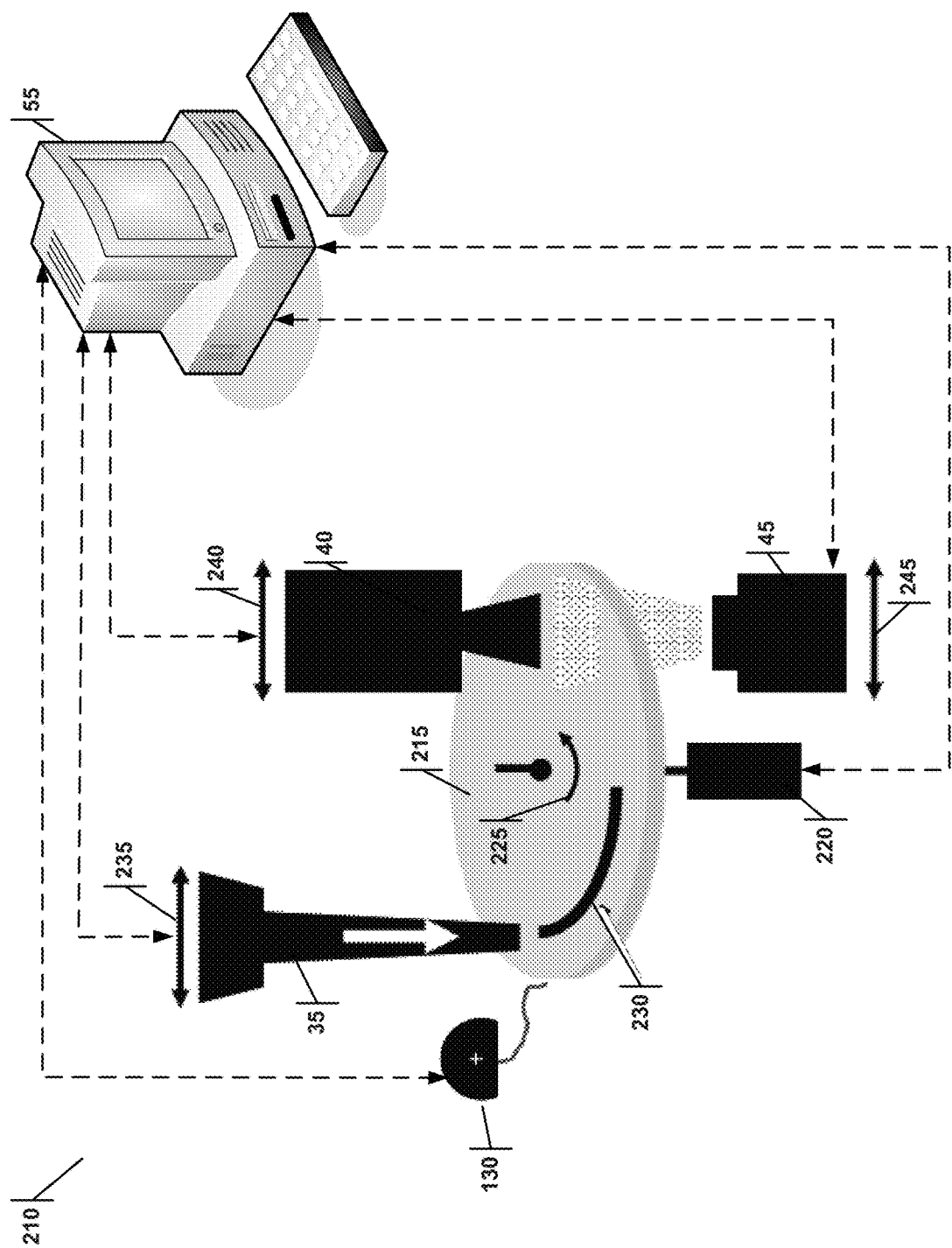
FIG. 3 illustrates a third embodiment of a particle image analyzer.

FIG. 3 shows a variant of the present invention that uses a flat platter instead of a roll of material. The transparent platter 215 used in the particle image analyzer 210 may be covered with an adhesive foil, or the particle image analyzer 210 may comprise an electrostatic generator 130 (shown as a positive generator) to impart a positive charge to a region of the load surface of the platter. The platter's rotation 225 can be achieved by a platter motor 220 with its rotor positioned perpendicularly to the platter surface. It should be noted that the platter motor 220 can have its rotor through the center of the platter 215, have the rotor connected to the center of the platter 215, or have the rotor spin the outer edge of the platter 215, which are all obvious variants without departing from the scope and spirit of this invention. These variants would be functionally equivalent, simply allowing for more flexibility in the size and speed of the platter motor 220 used.

In FIG. 3, the particle discharge nozzle 35 is moved laterally, indicated by arrows 235, across the load surface of the transparent platter 215. This lateral movement 235, combined with the platter rotation 225 regulated by the platter motor 220, results in a spiral particle deposition pattern 230 on the load or platter surface. The light source 45 adjacent to the opposite surface and image sensor 40 adjacent to the load surface also need to move laterally while the platter rotates to image all the particles. The lateral movement of the image sensor 40 across the load surface is indicated by the arrows 240, while the lateral movement across the opposite surface of the light source 45 is indicated by the arrows 245. Taking images on this rotating platter is like reading a gramophone recording, and the imaging the particles can occur at a different rotational speed than the speed at which deposition of particles occurs.

The particle image analyzer 210 may also comprise a processor 55 that can be used to control the particle discharge nozzle 35, the image sensor 40, the platter motor 220, and the light source 45. The processor 55 is connected to the image sensor 40 and receives images from the sensor 40. It can move the image sensor 40 laterally 240 and may also control the parameters of the image sensor 40 to calibrate the sensor and control the settings. The processor 55 can connect to the light source 45 and may move the light source 45 laterally 245, turn the light source 45 on and off, and/or optionally vary the light intensity of the light source 45. The processor 55 may be connected to the particle discharge nozzle 35 and may control the rate of deposition by the particle discharge nozzle 35 as well as the lateral movement 235 of the particle discharge nozzle 35. Finally, the processor 55 may control the platter motor 220 that in turn rotates the transparent platter 215, and may regulate the speed of the platter rotation 225 by controlling the platter motor 220.

Each of the above embodiments can be used with a single recording camera (as depicted for simplicity of representation in the figures, or by multiple cameras needed to obtain 3D images of particles, as space permits above the load surface, for complicated mechano-optical systems. It is also possible to place several cameras with corresponding illumination devices so that images of the very same particles can be simultaneously recorded under different enlargements, which is important for highly polydisperse samples with particle sizes ranging from millimeters down to microns.

In each of the above embodiments, an electrostatic generator 130 has been shown prior to or near particle deposition by the particle discharge nozzle 35. It should also be noted that the charge imparted may be positive or negative to achieve the effect of having the particles cling to the load surface.

Since any tape or platter can be easily covered with hydrophilic materials, it is possible to measure liquid, water-based samples by the very same system embodiments, where the regulated linear or rotational speed of the load surface can lead to a thin film of a sample obtained without any need for dilution. Aerosol or spray samples can also be deposited on the load surface of the present invention, thus allowing for measurement of particulate sizes in a diverse range of colloids as well.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A particle image analyzer comprising:
a transparent moving structure with a load surface and an opposite surface, wherein at least a portion of the load surface is constructed to adhere particles by either chemical adhesion and/or ionic attraction;
a particle discharge nozzle constructed to deposit particles on the load surface;
an image sensor positioned adjacent to the load surface and constructed to take images of the particles when they are adhered to the load surface and as they move past the image sensor;
a light source positioned adjacent to the opposite surface and constructed to illuminate the particles imaged by the image sensor, wherein the light from the light source defines an illumination path, wherein the path travels from the light source, through the opposite surface, through the load surface and to the image sensor.

2. The analyzer of claim 1, wherein the load surface comprises an adhesive.

3. The analyzer of claim 1, wherein the transparent moving structure comprises a transparent belt wrapped around a front roller and a back roller, the analyzer further comprising an electrostatic generator positioned prior to the particle discharge nozzle so as to impart a charge to a region of the load surface prior to the deposition of particles on the load surface.

4. The analyzer of claim 3, further comprising a ground to release the particles from the load surface.

5. The analyzer of claim 4, further comprising a particle recovery basin constructed to collect particles that have been released from the load surface.

6. The analyzer of claim 1, wherein the transparent moving structure comprises a transparent platter that is rotated by a platter motor.

7. The analyzer of claim 6, wherein the particle discharge nozzle is constructed to move laterally across the load surface of the platter.

8. The analyzer of claim 7, wherein the platter rotation and the lateral movement of the discharge nozzle create a spiral particle deposition pattern on the load surface.

9. The analyzer of claim 6, wherein the image sensor is constructed to move laterally across the load surface of the platter.

10. The analyzer of claim 6, wherein the light source is constructed to move laterally across the opposite surface of the platter.

11. The analyzer of claim 6, wherein the load surface comprises an adhesive.

12. The analyzer of claim 6, further comprising a positive electrostatic generator to impart a charge to a region of the load surface of the platter.

13. The analyzer of claim 1, further comprising a processor connected to the image sensor and constructed to receive images from the sensor and control the sensor parameters.

14. The analyzer of claim 13, wherein the image sensor is constructed to move laterally across the load surface, and the processor controls the lateral movement.

15. The analyzer of claim 13, wherein the processor is connected to the light source and constructed to control the light source.

16. The analyzer of claim 15, wherein the light source is constructed to move laterally across the opposite surface, and the processor controls the lateral movement.

17. The analyzer of claim 13, wherein the processor is connected to the particle discharge nozzle and constructed to control the deposition rate of the nozzle.

18. The analyzer of claim 17, wherein the particle discharge nozzle is constructed to move laterally across the load surface, and the processor controls the lateral movement.

19. The analyzer of claim 13, wherein the transparent moving structure comprises a motor connected to the processor, and wherein the processor controls the speed of the transparent moving structure.

20. The analyzer of claim 13, further comprising an electrostatic generator connected to the processor.

21. The analyzer of claim 20, further comprising a ground in contact with the transparent moving structure and controlled by the processor.

\* \* \* \* \*